United States Patent
Belkoff et al.

(10) Patent No.: US 9,743,971 B2
(45) Date of Patent: Aug. 29, 2017

(54) SMART SCREW-DRIVER FOR PREVENTING INADVERTENT SCREW STRIPPING IN BONE

(71) Applicant: THE JOHNS HOPKINS UNIVERSITY, Baltimore, MD (US)

(72) Inventors: Stephen Belkoff, Baldwin, MD (US); Evan Langdale, Baltimore, MD (US); Trevor Knight, Seattle, WA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 242 days.

(21) Appl. No.: 14/167,144

(22) Filed: Jan. 29, 2014

(65) Prior Publication Data
US 2014/0222012 A1 Aug. 7, 2014

Related U.S. Application Data

(60) Provisional application No. 61/757,962, filed on Jan. 29, 2013.

(51) Int. Cl.
*A61B 17/88* (2006.01)
*B25B 23/14* (2006.01)
(Continued)

(52) U.S. Cl.
CPC ...... *A61B 17/8875* (2013.01); *B25B 23/1405* (2013.01); *B25B 23/1425* (2013.01);
(Continued)

(58) Field of Classification Search
CPC . A61B 17/7076; A61B 17/7082; A61B 17/88; A61B 17/8875; B25B 23/1405; B25B 23/1425
See application file for complete search history.

(56) References Cited

U.S. PATENT DOCUMENTS

| 4,211,120 A | 7/1980 | Tambini |
| 7,565,844 B2 | 7/2009 | Crass et al. |

(Continued)

FOREIGN PATENT DOCUMENTS

WO 2009039497 A2 3/2009

OTHER PUBLICATIONS

Hsu, C., et al., "Increase of pullout strength of spinal pedicle screws with conical core: biomechanical tests and finite element analyses", Journal of Orthopaedic Research, vol. 23, Issue 4, pp. 788-794, Jul. 2005.

(Continued)

*Primary Examiner* — Larry E Waggle, Jr.
(74) *Attorney, Agent, or Firm* — Johns Hopkins Technology Ventures

(57) ABSTRACT

A programmable screw driver and method for affixing screws into bone is disclosed. The screw driver includes a torque sensor for measuring torsional input during screw insertion, a rotational motion sensor for measuring the rotation of the screw driver, and a microprocessor. Once a surgeon rotates a screw to be affixed to the bone, the torque sensor measures the torque and sends this information to the microprocessor. Once a predetermined torque level is attained, the microprocessor begins to measure subsequent rotation of the screw driver until a predetermined rotational limit, thereby causing a signal to be sent to alert the surgeon to stop tightening.

9 Claims, 2 Drawing Sheets

(51) Int. Cl.
*B25B 23/142* (2006.01)
*A61B 17/70* (2006.01)
*A61B 19/00* (2006.01)

(52) U.S. Cl.
CPC ....... *A61B 17/7076* (2013.01); *A61B 17/7082* (2013.01); *A61B 2019/301* (2013.01)

(56) References Cited

U.S. PATENT DOCUMENTS 7,900,524 B2 *  3/2011  Calloway ................ B25B 23/14
                                                   73/862.22
2008/0281332 A1 * 11/2008  Taylor ................ A61B 17/1626
                                                    606/104

OTHER PUBLICATIONS

Behring, J., et al., "Slippage Between Screwdriver and Bone Screw", Clinical Orthopaedics & Related Research, Nov. 2002—vol. 404—pp. 368-372.

* cited by examiner

SMART SCREW-DRIVER FOR PREVENTING INADVERTENT SCREW STRIPPING IN BONE

CROSS REFERENCE TO RELATED APPLICATIONS

This application claims the benefit of U.S. Provisional Patent Application No. 61/757,962 filed on Jan. 29, 2013, which is incorporated by reference, herein, in its entirety.

BACKGROUND OF THE INVENTION

Avoidance of over-tightening screws during fracture plate fixation or lag screw insertion is a goal in orthopaedics, as well as orthopaedic resident training In orthopaedics, screws are often inadvertently stripped when they are used to affix a fracture fixation plate to a broken bone. Screw stripping during internal fixation of displaced lateral malleolar fractures, for example, occurs in up to 88% of patients more than 50-years-old, whereas inadvertent and unrecognized screw stripping may occur at a rate of 20% in cortical bone. Determining an appropriate endpoint for screw insertion has been an elusive task. Much effort has been focused on identifying a torque limit for screw insertion. However, torque is a function of screw pitch, bone density and thickness, and bone-thread interfacial friction.

Torque is converted by means of the screw threads into screw tension, which provides the compressive force on the fixation plate to maintain fracture reduction. Experienced orthopaedic surgeons typically tighten screws to 86% of maximum torque clinically, which is presumably "two-fingers tight". Inserting screws beyond 70% of the maximum torque, at least in ovine tibiae, compromises pullout strength. Because peak torque depends on the material and geometric properties of bone, it is virtually impossible clinically, a priori, to know the peak torque for screw insertion in a given bone at a given location to stay below the 70% peak value. Once a screw is stripped, its pullout strength is reduced by more than 80% and may lead to loss of fracture reduction and implant failure.

An alternative to the torque-limiting method of tightening fasteners (screws) is the "turn-of-the-nut" method that uses a rotational limit and is the preferred method used in building construction. The method works by placing sample bolts in a proofing machine. The nut is tightened until snug and then rotated until the desired tension (specified by design) in the bolt is reached. The amount of rotation needed to achieve the design tension in the bolt, and thereby compression across the joint, is then applied to all nuts and bolts of the type proofed. In engineering applications, the nut and bolt are of the same material, and the bolt size is selected by design so that the load of a given bolt is well below its failure load.

In orthopaedic application, the bone assumes the role of the nut, and the screw size is dictated by the geometry of the bone, fracture and plate to be used. Because the failure properties of bone are much less than those of the screws, failure likely occurs in the threads cut into the bone. We assume that failure in bone threads is related to the rotation of the screw. Thus, once a screw is inserted so that the head is snug against the plate, there is a degree of rotation that will achieve optimal fixation without causing stripping and loss of screw purchase. However, many inexperienced surgeons cannot adequately determine when the head of the screw is seated against the plate or bone. The surgeon is also left to guess how much further to rotate the screw for optimal fixation.

Accordingly, there is a need in the art for an instrumented screw insertion tool that guides the surgeon to achieve optimal fixation.

SUMMARY

According to a first aspect of the present invention, a programmable screw driver for affixing screws into bone comprises a handle portion adapted to be held by a surgeon, a shaft portion for engaging a screw to be affixed, a torque sensor for measuring torsional input during screw insertion, the torque sensor operatively connected to the microprocessor, a rotational motion sensor for measuring the rotation of the screw driver, the rotational motion sensor operatively connected to the microprocessor such that rotation of the screw driver is measured and transmitted to said microprocessor, the microprocessor having a non-transitory computer readable medium, wherein, when executed by the microprocessor, causes the microprocessor to receive a signal from the torque sensor, determine whether the predetermined torque level has been reached, and when the predetermined torque level has been reached, causes the microprocessor to begin measuring subsequent rotation of the screw driver until a predetermined rotational limit has been reached, thereby causing a signal to be sent to alert the surgeon to stop tightening.

According to a second aspect of the present invention, a method for affixing a screw into bone comprises rotating a screw to be affixed to the bone by a programmable screw driver, sensing when a screw has reached a predetermined torque level, measuring subsequent rotation of the screw driver until a predetermined rotational limit has been reached, and alerting the surgeon to stop tightening.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Figure 1:
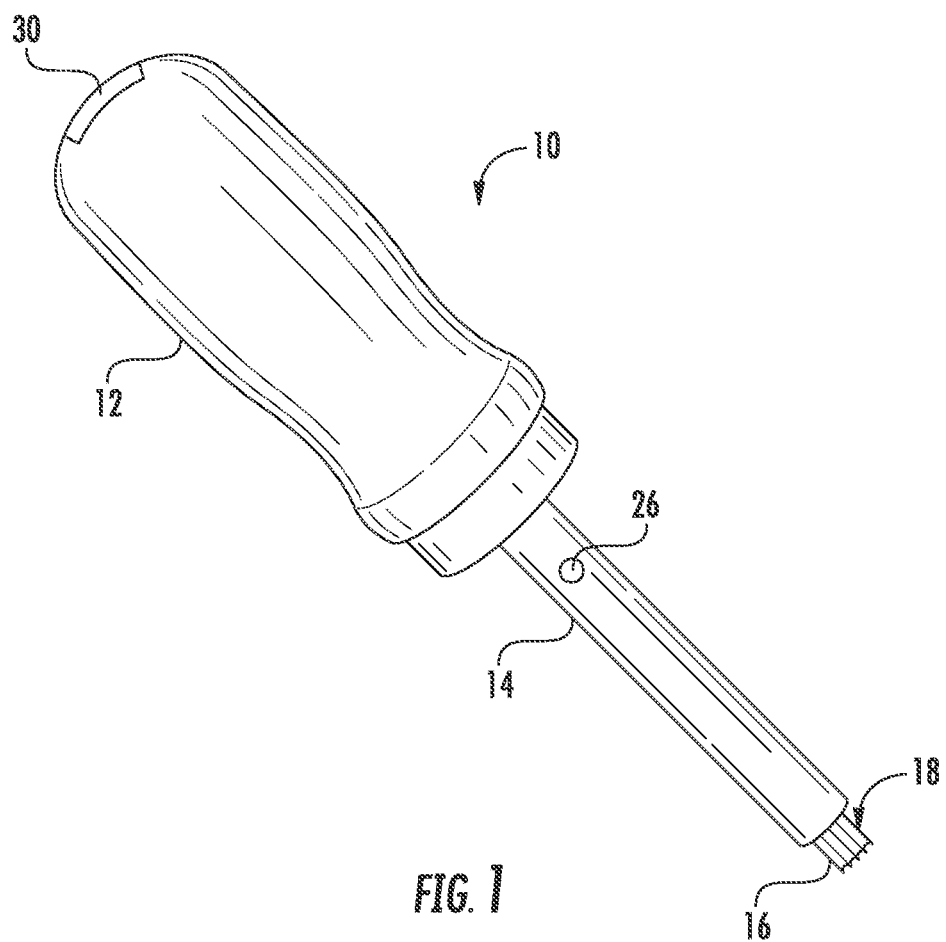
FIG. 1 illustrates a perspective view of an exemplary product according to the features of the present invention.

FIG. 1 illustrates a perspective view of a programmable screw driver 10 for affixing screws into bone. As illustrated in FIG. 1, the screw driver 10 includes a handle portion 12 and a shaft portion 14. The handle portion 12 is configured to be held in a hand of a surgeon for use in affixing the screws to bone. The shaft portion 14 is configured to engage the bone screw. For instance, a distal end 18 of the shaft can be configured with a particular shaped region 16, configured to couple with a pattern in the head of the bone screw. This engagement allows the screw to be turned and tightened to the desired torque level. As illustrated in FIG. 1, the screw driver 10 includes a torque sensor 26 positioned on the shaft portion 14. The torque sensor 26 measures torsional input. The screw driver 10 can also include a USB port 30 or other port for entering or obtaining data from the device. The port can also take the form of any other suitable port protocol known to or conceivable by one of skill in the art.

Figure 2:
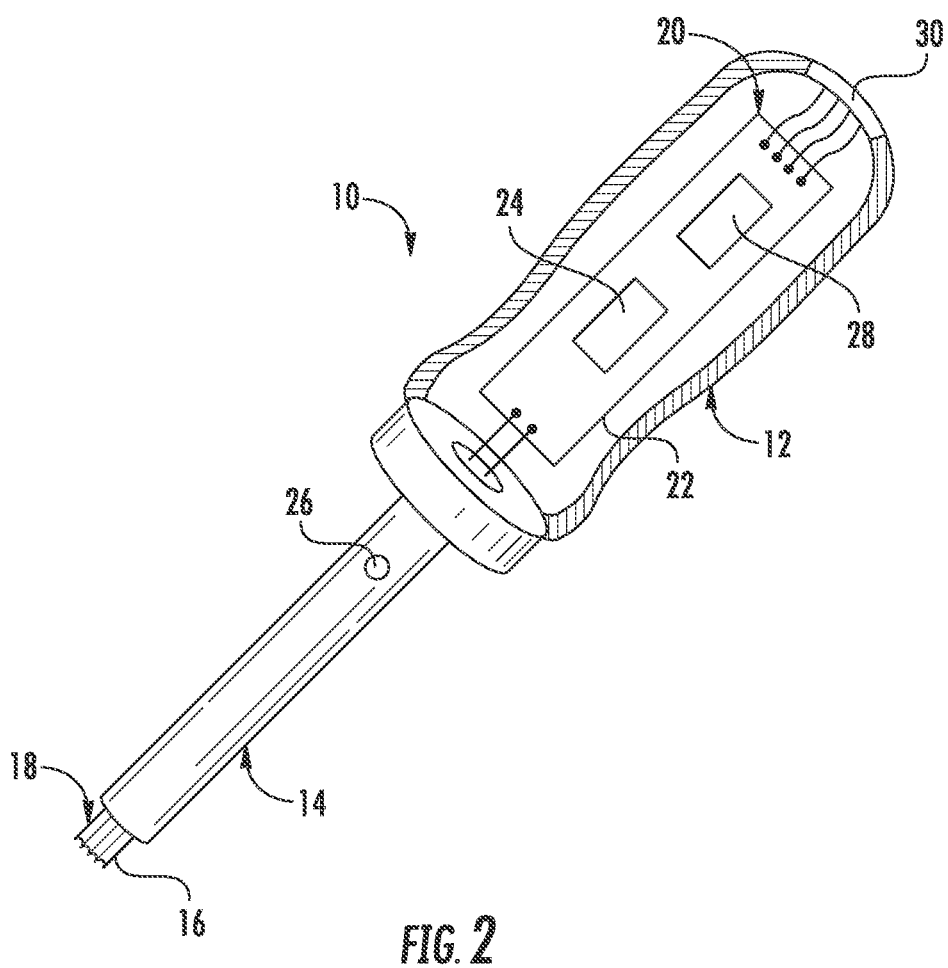
FIG. 2 illustrates a partially sectional perspective view of an exemplary product according to the features of the present invention.

With reference to FIG. 2, a partially sectional view of a programmable screw driver 10 for affixing screws into bone is illustrated. In particular, the programmable screw driver 10 of the present invention is adapted to be used when affixing a bone affixation plate to a broken bone by way of screws with minimal stripping of the screw. However, the present invention may also be used in connection with lag screws used to apply compressive force across fracture surfaces.

In one, non-limiting, embodiment, the screw driver 10 includes a handle portion 12 adapted to be held by a surgeon and a shaft portion 14 for engaging a screw to be affixed. The shaft portion 14 preferably includes a male, grooved portion 16 at its distal end 18 to mate with a female, recessed portion disposed in the head of the screw (not shown). Within the handle portion 12 of the screw driver 10 is an interior 20. The interior 20 of the handle portion 12, preferably, houses the electronics for operation of the screw driver 10. However, the shaft portion 14 may also house the electronics for operation of the screw driver 10, depending on application and design preference.

In the preferred embodiment, the interior 20 houses a circuit board 22 including a microprocessor 24 having a non-transitory computer readable medium. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The microprocessor 24 is operatively connected to a torque sensor 26 and a rotational motion sensor 28. The torque sensor 26 measures torsional input and sends this information to the microprocessor to assess when a predetermined torque level is attained. That is, the microprocessor 24 has a non-transitory computer readable medium, wherein, when executed by the microprocessor 24, causes the microprocessor 24 to receive a signal from the torque sensor 26 to determine whether the predetermined torque level has been reached. The predetermined torque level relates to when the screw is seated against a bone affixation plate or when the head of the screw is adjacent the bone when using lag screws, and may be determined experimentally. Preferably, the torque sensor 26 is a strain gauge but may be other types of devices used for measuring torque.

Once the predetermined torque level is attained, the microprocessor 24 begins to measure subsequent rotation of the screw driver 10 by way of the rotational motion sensor 28 until a predetermined rotational limit has been reached. In this way, the rotational motion sensor 28 measures rotation of the screw driver 10 and transmits this information to the microprocessor 24. In experiments, the optimal rotational limit was found to be 180 degrees. However, the screw driver 10 may be programmed with other rotational limits, depending upon application and design preference. In the preferred embodiment, the rotational motion sensor 28 is a gyroscope, but other sensors are also possible, depending upon application and design preference.

Once the predetermined rotational limit is reached, the microprocessor causes a signal to be sent to alert the surgeon to stop tightening. The alert mechanism may include, but is not limited to, a readout, buzzer, light or vibration. Optionally, a connection port, such as a USB port 30, may be included to transfer data to a remote computer for further processing, such as for research or quality control purposes. The connection port 30 is operatively connected to the microprocessor 24.

According to the features of the present invention, a surgeon may use the device to more accurately affix a screw into bone. The device indicates to the surgeon when to stop tightening bone screws in order to prevent screw stripping and subsequent loss of fracture fixation.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A programmable screw driver for affixing screws into bone, comprising:
   a handle portion adapted to be held by a surgeon;
   a shaft portion for engaging a screw to be affixed;
   a torque sensor for measuring torsional input during screw insertion, said torque sensor operatively connected to a microprocessor;
   a rotational motion sensor for measuring rotation of the screw driver, said rotational motion sensor operatively connected to said microprocessor such that rotation of the screw driver is measured and transmitted to said microprocessor;
   said microprocessor having a non-transitory computer readable medium, wherein, when executed by the microprocessor, causes the microprocessor to receive a signal from said torque sensor, determine whether a predetermined torque level has been reached, and when the predetermined torque level has been reached, causes the microprocessor to begin measuring subsequent rotation of the screw driver until a predetermined rotational limit has been reached, thereby causing a signal to be sent to alert the surgeon to stop tightening.

2. The screw driver of claim 1, wherein the predetermined rotational limit is 180 degrees.

3. The screw driver of claim 1, wherein the torque sensor is disposed within the shaft portion.

4. The screw driver of claim 1 wherein the torque sensor comprises a strain gauge.

5. The screw driver of claim 1 wherein the shaft portion includes a distal end having geometry configured to engage geometry on a head of a bone screw.

6. The screw driver of claim 1 further comprising a connection port.

7. The screw driver of claim 6 wherein the connection port further comprises a USB port.

8. The screw driver of claim 6 wherein the connection port is disposed in the handle portion.

9. The screw driver of claim 6 wherein the connection port is in communication with the microprocessor.

\* \* \* \* \*